(12) United States Patent
Okawa et al.

(10) Patent No.: US 6,981,868 B2
(45) Date of Patent: Jan. 3, 2006

(54) DENTAL FILLING INSTRUMENT AND ATTACHMENT THEREFOR

(75) Inventors: Shinichi Okawa, Kyoto (JP); Kazunari Matoba, Kyoto (JP); Chihiro Kobayashi, Ichikawa (JP); Takatomo Yoshioka, Tokyo-to (JP)

(73) Assignee: J. Morita Manufacturing Corporation, Kyoto (JP)

( * ) Notice: Subject to any disclaimer, the term of this patent is extended or adjusted under 35 U.S.C. 154(b) by 157 days.

(21) Appl. No.: 10/008,078

(22) Filed: Nov. 8, 2001

(65) Prior Publication Data

US 2002/0086264 A1    Jul. 4, 2002

(30) Foreign Application Priority Data

Nov. 9, 2000    (JP) .............................. 2000-341822

(51) Int. Cl.
*A61C 5/02*    (2006.01)
*A61C 5/04*    (2006.01)

(52) U.S. Cl. ............................ 433/81; 433/32; 433/89; 433/224; 222/326; 604/154

(58) Field of Classification Search .................. 433/32, 433/80, 81, 89, 90, 224; 272/326, 333, 638, 272/639, 63, 52, 146.1, 146.2, 146.5; 604/154, 604/155

See application file for complete search history.

(56) References Cited

U.S. PATENT DOCUMENTS

| | | | | |
|---|---|---|---|---|
| 4,704,088 | A | * | 11/1987 | Newman ...................... 433/81 |
| 4,759,712 | A | * | 7/1988 | Demand ...................... 433/32 |
| 4,950,246 | A | * | 8/1990 | Muller ...................... 604/154 |
| 6,050,450 | A | * | 4/2000 | Gardos ....................... 222/333 |
| 6,171,276 | B1 | * | 1/2001 | Lippe et al. .................. 604/67 |
| 6,312,254 | B1 | * | 11/2001 | Friedman .................... 433/32 |
| 6,500,001 | B2 | * | 12/2002 | Horth et al. .................. 433/89 |
| 6,605,067 | B1 | * | 8/2003 | Larsen ....................... 604/192 |

FOREIGN PATENT DOCUMENTS

JP    H1-40621    8/1989
WO    WO 82/03761    11/1982

* cited by examiner

*Primary Examiner*—John J Wilson
(74) *Attorney, Agent, or Firm*—Koda & Androlia (57) ABSTRACT

A dental injecting apparatus for injecting a dental filler and a dental tool attached to such a dental injecting apparatus. The apparatus includes: an injection rod for injecting a dental filler; an injection rod driver for performing a dental filler injecting operation that causes the injection rod to move in a dental filler injecting direction by using the force of a power source; and a controller for controlling the dental filler injecting operation of the injection rod driver.

18 Claims, 9 Drawing Sheets

DENTAL FILLING INSTRUMENT AND ATTACHMENT THEREFOR

CROSS-REFERENCE TO RELATATED APPLICATION

This application is based upon application No. 2000-341822 filed in Japan, the contents of which are hereby incorporated by reference.

BACKGROUND OF THE INVENTION

1. Field of the Invention

The present invention relates to a dental filling instrument and an attachment therefor, and particularly relates to a dental filling instrument used to inject a filler into a tooth cavity in dental treatment and an attachment that can be attached to the dental filling instrument.

2. Description of the Related Arts

Heretofore, various dental filling instruments for injecting a dental filler such as gutta-percha or resin into a tooth cavity (such as a root canal or a defective part of a tooth) have been proposed for dental treatment.

Japanese Examined Laid-Opened Patent Publication No. HEI 1-40621 (International Publication Number: WO82/03761, International Application Number: PCT/US81/00589), for example, discloses a syringe-type filling instrument having a push rod to be thrust forward to extrude a filler in a state softened by heating with a heater from the tip of a needle.

Figure 1:
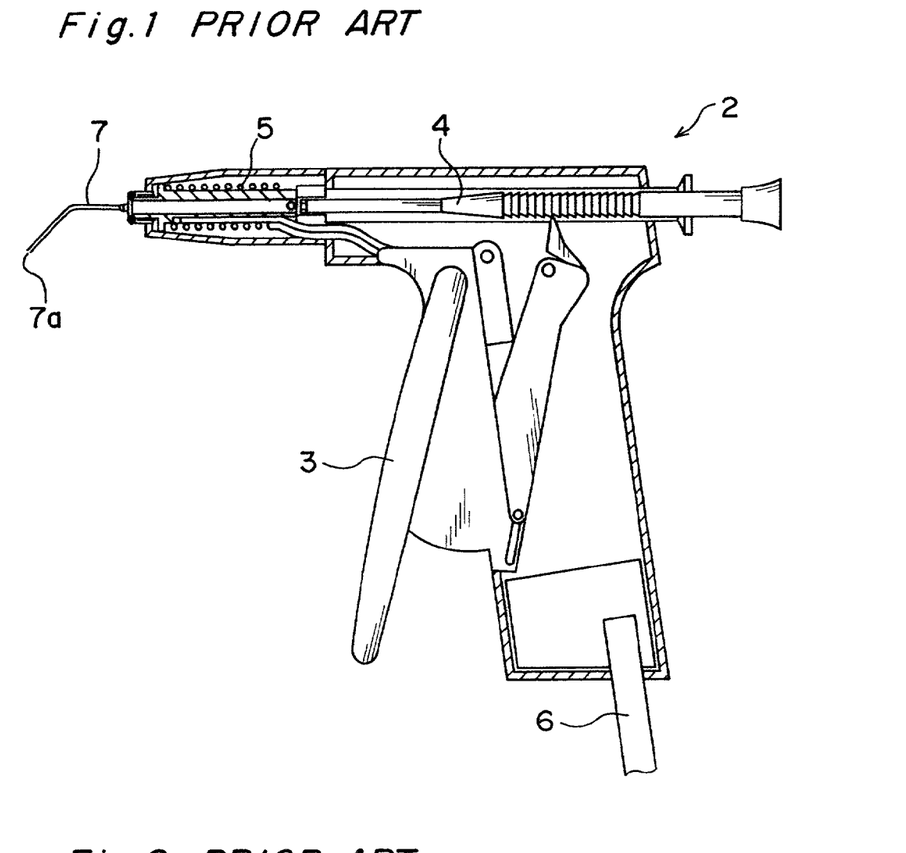
FIG. 1 is a sectional view showing a conventional dental filling instrument.

A gun-type filling instrument 2 as shown in FIG. 1 is designed to thrust forward a push rod 4 by means of a ratchet mechanism when a lever 3 is pulled, thereby extruding a filler in a state softened by heating with a heater 5 from a tip 7a of a needle 7.

Such conventional filling instruments, however, require application of a large force to the push rod or the lever to extrude the filler. It is therefore not easy to hold the filling instrument so as not to displace the needle tip from a filler-pouring position even when a larger force is applied to the push rod or lever with a finger. For this reason, the user of such a filling instrument is required to become skillful. If the filler is not sufficiently softened, a larger force is required to extrude the filler and, hence, it is difficult to perform the operation of delicately moving the needle tip position as the filler-pouring operation proceeds and the operation of extruding the filler at the same time. Further, at the same time with the operation of extruding the filler, the operator needs to lift the needle tip gradually while sensing a subtle pressure of raising the needle tip received from the filler injected. Thus, the conventional instruments require the operator to perform complicated operations while paying attention to many different points.

Figure 2:
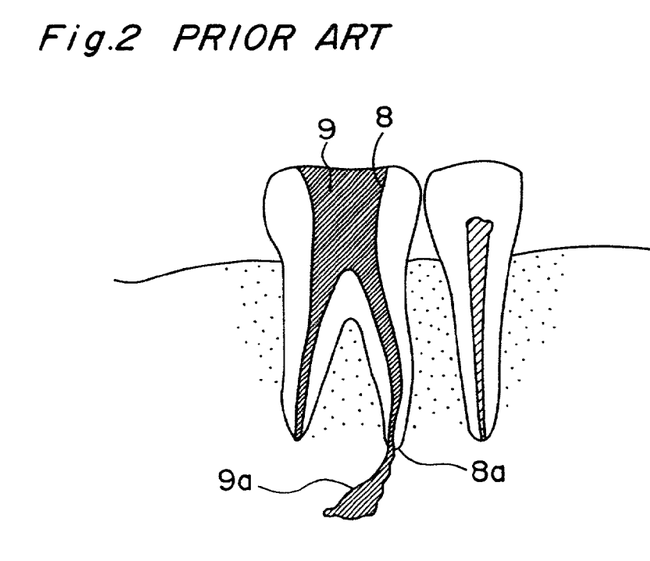
FIG. 2 is a schematic view illustrating a root canal treatment using the conventional dental filling instrument.

When a root canal 8 is to be filled with a filler 9 as shown in FIG. 2, filler 9a may overflow from an apical part Ba if the filler is extruded in an excessive amount or abruptly. It is pointed out that such an overflowed filler 9a leads to unsatisfactory convalescence; for example, filler 9a causes a pain when the patient is subjected to percussion or it takes a longer time for filler 9a to be completely absorbed.

If the filler is cooled during the extrusion thereof from the needle, it is possible that the filler cannot be filled closely into a tooth cavity or that the filler adheres to the needle and hence is withdrawn from the tooth cavity along with the needle when the needle is withdrawn from the tooth cavity after the injection of the filler.

In an operating method including an insertion of a solid filler into a root canal, a cut of the filler to a predetermined length and an injection of a softened filler, it is possible that the solid filler is cut by heating with a needle attached to a filling instrument. Such a cutting operation is difficult if the needle is cool.

A root canal filling method has been proposed which includes an insertion of a solid filler in the form of an elongate tapered stick such as a master point or an accessory point into an apical foramen to plug it and a cut off an unnecessary portion of the stick-shaped filler other than the tip portion plugging the apical foramen by instantaneously fusing the filler (for about one second) with a heated leading end of an attachment called "spreader". There has been proposed another root canal filling method which uses an attachment called "plugger" to press a filler injected into a root canal against the root canal in order to fill the root canal with the filler air-tightly. When such a root canal filling method is used before or after the injection of a filler, an instrument used in one operation needs to be replaced by another to be used in another operation. Such an exchange makes the filling operation cumbersome. Further, if instruments used in respective operations are different in size, shape, weight or the like from each other, a feel or touch in one operation is different from that in another operation, making each operation more difficult.

Still another filling method uses different fillers for different parts of a root canal; for example, a filler of the low-temperature-melting type which melts at a low temperature is used in an apical part requiring tight sealing, while a common filler of the high-temperature-melting type which melts at a high temperature is used in a main root canal portion. In this case, provision of different filling instruments for respective fillers having different properties raises a problem of cost. Further, there is a need for adjusting and operating filling instruments respectively, resulting in a cumbersome and complex operation with low efficiency.

SUMMARY OF THE INVENTION

Accordingly, it is an object of the present invention to provide a dental filling instrument capable of filling a tooth cavity with a dental filler more easily and an attachment attachable to the dental filling instrument.

In order to achieve the above object, according to one aspect of the present invention, there is provided a dental filling instrument comprising: a push rod for extruding a dental filler; a push rod driving device for performing a dental filler extruding operation that causes the push rod to travel in a dental filler extruding direction by utilizing power of a power source; and a control device for controlling the dental filler extruding operation of the push rod driving device.

The dental filling instrument is of a type adapted to extrude a dental filler by means of a push rod. The dental filling instrument includes the push rod driving device and the control device. The push rod driving device is capable of performing the dental filler extruding operation that causes the push rod to travel in a dental filler extruding direction by utilizing power of a power source. The control device controls the dental filler extruding operation of the push rod driving device.

In the above construction, the push rod driving device may be appropriately configured in different embodiments. For example, the power of the power source may be transmitted to the push rod either directly or through a power transmission system comprising an appropriate combination of a gear, rack, thread, lever, link mechanism and the like. As the power source may be used any one of various existing actuators or human power, i.e., the operating power of an operator's hand. Examples of suitable actuators include, but not limited to, various motors such as a DC motor, AC motor and pulse motor, hydraulic cylinders using oil or water, pneumatic cylinders, and air turbines. If the push rod driving device is hand-operated, it may be charged with the operating force of a human hand by means of a spring, for example.

With the construction described above, the push rod is moved by the power of the power source and, hence, any operation requiring a large force for extruding the filler (for example, the operation of thrusting the push rod or the lever) becomes unnecessary.

In the above construction, the control device may be of any appropriate configuration for controlling the operation of the push rod driving device. For example, the control device may be configured to control the ON-OFF operation of the power source. Alternatively, the control device may be configured to control a switching mechanism or reduction gear mechanism provided in the power transmission system of the push rod driving device.

According to the construction described above, the traveling of the push rod is controlled by the control device. This feature makes it possible to control the amount of a filler to be injected, filler injection speed and the like without the necessity of adjusting an operator's hand operation of moving the push rod (for example, the operation of thrusting the push rod or the lever), thereby easing the required operations. Thus, the dental filling instrument is capable of realizing easier filling of a dental filler.

Where a dental filler that can be softened by heating (gutta-percha for example) is used in the above construction, heating device is disposed around a cylinder to heat and soften the dental filler and the filler thus softened is extruded by the push rod.

Preferably, the control device includes a traveling speed control section for controlling traveling speed of the push rod.

This feature makes it possible to extrude a filler at a desired speed by controlling traveling speed of the push rod. Thus, it is possible to fill a tooth cavity with a filler at speed suitably adjusted to different conditions including filler characteristic, part to be filled, filling method, and the like.

Preferably, the control device includes a traveling distance control section for controlling distance which the push rod travels.

This feature makes it possible to extrude a filler in a desired amount by controlling the push rod so that it travels appropriate distance. Thus, it is possible avoid excessive filling. For example, in plugging an apical part with a filler, extruding the filler in a required amount makes it possible to avoid overflow of the filler from the apical part or limit the amount of the filler overflowed, thereby minimizing the overflow of the filler. In filling a whole root canal with a filler, it is possible to avoid filling of the filler in an amount greater than necessary, hence, prevent the filler from overflowing from an upper part of the root canal.

Preferably, the control device includes a traveling time control section for controlling traveling time of the push rod.

This feature makes it possible to prevent the filler extruding operation from being performed for a time period longer than a predetermined time period by controlling the push rod so that it travels for a predetermined time period. Thus, the amount of the filler to be extruded will not exceed a fixed amount. Further, since the extrusion time is limited and the filler extruding operation stops automatically, there is no need to perform the operation of stopping the filler extrusion. This advantage allows the operator to concentrate his or her attention to the filling operation.

Preferably, the dental filling instrument includes an injection condition setting device for setting an amount of the dental filler to be injected and setting injection speed of the dental filler. The control device establishes a target value of push rod traveling time based on the amount thereof and the injection speed set by the injection condition setting device, thereby controlling the dental filler extruding operation of the push rod driving device.

With this feature, a target value of push rod traveling time is automatically established based on the injection amount and injection speed set, thereby controlling the push rod traveling time. In the case where the push rod traveling speed is variable, it is possible to establish a target value of traveling time according to varying push rod traveling speed. If the injection amount and injection speed, which usually can be easily determined from a part into which the filler is to be injected or an injecting method employed, are set, optimized injection time and operation time can be established automatically. In this case there is no need to establish the injection time that is found from cumbersome calculation and, hence, the dental filling instrument can be used conveniently.

Preferably, the dental filling instrument includes an injection condition setting device for setting at least one of an amount of the dental filler to be injected, filler injection time and injection speed of the dental filler. The control device controls the dental filler extruding operation of the push rod driving device based on the injection condition set by the injection condition setting device.

This feature makes it possible to control the filler extruding operation so as to meet the injection condition set by the user. Since the injection condition can be changed, the dental filling instrument finds wider application.

Preferably, the dental filling instrument includes an injection condition display device for displaying at least one of an amount of the dental filler to be injected, filler injection time and injection speed of the dental filler.

This feature allows the user to know the injection condition more easily through the injection condition display device.

Preferably, the control device includes an extruding operation switch and a control section responsive to the extruding operation switch. When the extruding operation switch is in an ON state, the control section responsive to the extruding operation switch permits the push rod driving device to perform the dental filler extruding operation. On the other hand, when the extruding operation switch is in an OFF state, the control section forcibly inhibits the push rod driving device from operating.

In the above construction, an arrangement may be employed such that the filler can be extruded only when the extruding operation switch is ON but cannot be extruded when the extruding operation switch is OFF. The control section responsive to the extruding operation switch takes precedence over the traveling distance control section, traveling time control section and the like. This means that when the extruding operation switch is turned OFF, the control section responsive to the extruding operation switch forcibly stops the traveling of the push rod even if the predetermined traveling distance or traveling time is not reached.

This feature makes it possible to start or stop the filler extruding operation in response to the ON-OFF operation of the extruding operation switch, thereby allowing the user to perform the filling operation intuitively. In addition, it is possible to operate the extruding operation switch with a small force. Thus, the filling operation becomes easier.

Preferably, the push rod driving device is capable of performing a push rod returning operation that causes the push rod to travel in a direction opposite to the dental filler extruding direction by utilizing the power of the power source. The control device includes a returning operation switch and a control section responsive to the returning operation switch. When the returning operation switch is in an ON state, the control section responsive to the returning operation switch forcibly inhibits the push rod driving device from performing the dental filler extruding operation while permitting the push rod driving device to perform the push rod returning operation.

This feature makes it possible to return the push rod by merely turning ON the returning operation switch and, hence, it is no longer necessary for the user to return the push rod by hand. Thus, the dental filling instrument with this feature is convenient.

Preferably, the control device includes an extrusion stop control section for causing the push rod driving device to perform the returning operation for a predetermined time period immediately after the dental filler extruding operation of the push rod driving device has been stopped.

Even if the dental filler extruding operation is merely stopped, the dental filler continues to be extruded for a while after the extruding operation has been stopped. With the above feature, however, it is possible to prevent the dental filler from being extruded immediately after the dental filler extruding operation has been stopped. Accordingly, the filling operation is facilitated. Particularly where control is performed to fill a fixed amount of the filler, the accuracy in controlling the filling amount can be advantageously improved.

Preferably, the push rod driving device is capable of performing a push rod returning operation that causes the push rod to travel in a direction opposite to the dental filler extruding direction by utilizing the power of the power source. The control device includes a terminating point detection device, a starting point detection device, and a push rod traveling range control section. The terminating point detection device detects the push rod reaching a first predetermined position in the dental filler extruding direction. The starting point detection device detects the push rod reaching a second predetermined position in a direction opposite to the dental filler extruding direction. The push rod traveling range control section forcibly inhibits the push rod driving device from performing the dental filler extruding operation when the terminating point detection device detects the push rod reaching the first predetermined position. On the other hand, the push rod traveling range control section forcibly inhibits the push rod driving device from performing the push rod returning operation when the starting point detection device detects the push rod reaching the second predetermined position.

This feature enables the push rod to travel between the first predetermined position and the second predetermined position. Thus, it is possible to prevent the push rod from being continuously pushed in the extruding direction or pulled in the returning direction, hence, to prevent the instrument from breaking, whereby safety is ensured.

The dental filling instrument with each of the features described above may comprise a main body from which the filler is extruded, and a separate device connected to the main body through a connection cable. In this case it is possible to dispose each of the push rod driving device, control device, injection condition setting device and injection condition display device in one of the main body and the separate device or both.

Preferably, the dental filling instrument includes a housing shaped to allow a user to hold it with one hand. All the other components (namely, components other than the housing including the push rod driving device, control device, injection condition setting device, injection condition display device and other components) are provided in one of a location which corresponds to an inside of the housing, and a location which corresponds to an outer surface of the housing.

With this feature, the dental filling instrument is wholly rendered compact and has an integral configuration. Since this configuration is a cordless configuration free from any trouble in handling the connection cable or the like, the dental filling instrument can be freely operated as desired by the user holding it and hence offers improved operability.

According to another aspect of the present invention, there is provided a dental filling instrument for extruding a dental filler in a heated state from a tip of a needle attached to a needle fitting portion thereof, comprising: a heating device for heating the needle up to a temperature at which the dental filler is softened, the heating device being disposed at one of the needle fitting portion and a location adjacent to the needle fitting portion; a heating temperature setting device for setting the temperature up to which the needle is heated by the heating device; and a heating control device for controlling a heating operation of the heating device based on the temperature set by the heating temperature setting device.

In the construction described above, the needle attached to the dental filling instrument is heated by the heating device. The heating of the needle is appropriately controlled based on the temperature set by the heating temperature setting device.

In the above construction, the heating device may be variously configured in different embodiments. For example, the heating device may be configured to transfer heat generated by the heating device to the needle or to cause the needle to generate heat based on Joule heat caused by electric current by passing electric current through the needle from the heating device or by applying magnetic flux that is variable with time to the needle to generate eddy current. Though the heating device may be configured to serve also as a filler heating device for softening the dental filler, the heating device is preferably configured to be separate from and independent of the filler heating device. This preferable configuration is capable of controlling the temperature of the needle independently of the heating control for the dental filler, thereby facilitating the heating temperature control for the needle.

In the above construction, the heating temperature setting device may be configured to set a temperature directly or to allow setting of a temperature suited to the type of dental filler selected. In the case where the heating temperature setting device does not set a temperature or a special setting is made, the heating device may be configured not to heat the needle. In this case it is possible that only the dental filler is heated, while the needle is not heated.

This construction makes it possible to heat the needle based on the temperature set according to the softening temperature of a dental filler and inject the dental filler in a sufficiently softened state from the needle into a desired part. Thus, the dental filling instrument enables the filling of the dental filler more easily.

Preferably, the dental filling instrument includes a heating temperature display device for displaying the heating temperature set by the temperature setting device.

This feature allows the user to confirm the set heating temperature at the time of heating temperature setting or during the heating of the needle, thereby affording convenience to the user.

The dental filling instrument with each of the features described above may comprise a main body from which the filler is extruded, and a separate device connected to the main body through a connection cable. In this case it is possible to locate each of the heating device, heating temperature setting device, heating control device and heating temperature display device in one of the main body and the separate device or both.

Preferably, the dental filling instrument includes a housing shaped to allow a user to hold it with one hand. All other components (namely, components other than the housing including the heating device, heating temperature setting device, heating control device, heating temperature display device and other components) are provided in one of a location which corresponds to an inside of the housing, and a location which corresponds to an outer surface of the housing.

With this feature, the dental filling instrument is wholly rendered compact and has an integral configuration. Since this configuration is a cordless configuration free from any trouble in handling the connection cable or the like, the dental filling instrument can be freely operated as desired by the user holding it and hence offers improved operability.

According to still another aspect of the present invention, there is provided a dental filling instrument comprising: a main body; and a needle fitting portion, provided in the main body, for attaching a needle, so as to extrude a dental filler from a tip of the needle, wherein the needle fitting portion is capable of being fitted with an attachment of one of the spreader type and the plugger type.

Namely, the construction thereof allows a spreader- or plugger-type attachment to be fitted to the needle fitting portion of the dental filling instrument. When the spreader-type attachment is fitted to the needle fitting portion, the user becomes capable of cutting a master point or accessory point inserted into a root canal to plug an apical part by fusing an upper portion thereof with the attachment heated at its leading end. Alternatively, when the plugger-type attachment is fitted to the needle fitting portion, the user becomes capable of depressing a plug inserted into a root canal with the leading end of the plugger-type attachment so that the plug adheres to the root canal by pressure.

With this construction the user is allowed to operate the spreader- or plugger-type attachment while holding the dental filling instrument as well as to perform the filling of a dental filler with a touch similar to the spreading or plugging operation. Further, it is possible to reduce the number of appliances to be used by using common appliances in both of these operations, hence, facilitate the choice of appliances. Thus, the dental filling instrument makes it possible to fill the filler more easily.

Preferably, a heater is included in one of the needle fitting portion and a portion adjacent thereto.

This feature makes it possible to heat the attachment fitted to the needle fitting portion of the dental filling instrument without using a burner or the like, thereby affording convenience to the user. Also, heating temperature control is easy. For example, by merely passing electric current through the heater for a given time it is possible that the attachment is heated to a predetermined temperature.

Preferably, the needle fitting portion can be fitted with an attachment having a first end attached to the needle fitting portion and a second end and defining a through-hole extending therethrough from the first end to the second end.

This feature is capable of extruding the dental filler from the second end of the spreader- or plugger-type attachment defining the through-hole fitted to the needle fitting portion. Since the dental filling instrument is capable of performing the spreading or plugging operation as well as the operation of filling the dental filler, it offers improved operating efficiency.

Preferably, the needle fitting portion is capable of being fitted with an attachment formed from a superelastic alloy.

Since the spreader- or plugger-type attachment formed from a superelastic alloy (nickel titanium alloy, for example) exhibits sufficient flexibility, this feature allows the attachment to be easily inserted into a root canal along its curved wall.

The dental filling instrument with each of the features described above may comprise a main body from which the filler is extruded, and a separate device connected to the main body through a connection cable. In this case it is possible to locate each component of the dental filling instrument in one of the main body and the separate device or both.

Preferably, the dental filling instrument includes a housing shaped to allow a user to hold it with one hand. All other components are provided in one of a location which corresponds to an inside of the housing, and a location which corresponds to an outer surface of the housing.

With this feature, the dental filling instrument is wholly rendered compact and has an integral configuration. Since this configuration is a cordless configuration free from any trouble in handling the connection cable or the like, the dental filling instrument can be operated freely as desired by the user holding it and hence offers improved operability.

According to still another aspect of the present invention, there is provided an attachment of one of the spreader type and the plugger type, comprising: a body; and an attaching portion, provided in the body, for attaching to a needle fitting portion of a dental filling instrument adapted to extrude a dental filler from a tip of a needle attached to the needle fitting portion thereof.

With the attachment of the above construction fitted to the dental filling instrument, the user is allowed to perform the operation of cutting a root canal filler or pressure-bonding the filler to the root canal as well as to perform the filling of a dental filler with a touch similar to the cutting or pressure-bonding operation. Further, it is possible to reduce the number of appliances to be used by using common appliances in both of the operations, hence, facilitate the choice of appliances. Thus, it is possible to fill the filler more easily.

Preferably, the attachment has a first end attached to the needle fitting portion and a second end and defines a through-hole extending therethrough from the first end to the second end.

Preferably, the attachment is made of a superelastic alloy.

According to still another aspect of the present invention, there is provided a dental filling instrument comprising: a heating and extruding device for heating a dental filler and extruding the same; and a filler storage device for storing a plurality of dental fillers, each of whish is the dental filler, and for selectively supplying the plurality of dental fillers thus stored to the heating and extruding device.

With this construction, an appropriate one of the plurality of dental fillers stored in the filler storage device can be selected for use. Since there is no need to load the instrument with additional dental filler in the middle of a series of operations using plural dental fillers, it is possible to improve the operating efficiency. Thus, the dental filling instrument makes it possible to fill the dental filler more easily.

The filler storage device may employ various types of filler selective supply system. For example, the filler storage supply device may employ a sliding system. Specifically, the filler storage device includes a plurality of storage sections for storing the dental fillers therein. The filler storage device is slidably supported so that each of the storage sections is selectively located at a communicating position providing communication between each of the storage section and the heating and extruding device.

This feature is capable of selecting a filler to be used by causing the filler storage device to slide so that a storage section storing the desired filler becomes located at the communicating position.

The filler storage device may employ a revolver system. Specifically, the filler storage device includes a plurality of storage sections for storing the dental fillers therein. The filler storage device is rotatably supported so that each of the storage sections is selectively located at a communicating position providing communication between each of the storage section and the heating and extruding device.

This feature is capable of selecting a filler to be used by causing the filler storage device to rotate so that a storage section storing the desired filler becomes located at the communicating position.

The filler storage device may employ another system. Specifically, the filler storage device includes a plurality of storage sections for storing the dental fillers therein, and a communicating section for providing selective communication between each of the storage sections and the heating and extruding device.

This feature allows a storage section storing a desired filler therein to communicate with the heating and extruding device through the communicating section, thereby transferring the desired filler from the storage section to the heating and extruding device. Thus, it is possible to select a filler to be used.

Preferably, each of the storage sections is configured to store a plurality of fillers and to transfer the fillers one by one to the heating and extruding device. This feature makes it possible to reduce the number of times of filler loading, thereby making the filling operation more efficient.

Preferably, the dental filling instrument includes heating and extruding condition setting device for setting at least one of heating and extruding conditions including temperature at which the heating and extruding device heats each of dental fillers, heating time and extruding amount so as to match the dental filler supplied from the filler storage device to the heating and extruding device.

In the dental filling instrument with the above feature, the heating and extruding condition setting device is configured to set the heating and extruding condition for each of the storage sections of the filler storage device, for example.

With this feature, at least one heating and extruding condition is automatically set to match the dental filler to be used and, hence, the filling operation becomes simplified.

Preferably, the dental filling instrument includes a housing shaped to allow a user to hold it with one hand. All other components (namely, components other than the housing including the push rod driving device, control device, injection condition setting device, injection condition display device and other components) are provided in one of a location which corresponds to an inside of the housing, and a location which corresponds to an outer surface of the housing.

With this feature, the dental filling instrument is wholly rendered compact and has an integral configuration. Since this configuration is a cordless configuration free from any trouble in handling the connection cable or the like, the dental filling instrument can be freely operated as desired by the user holding it and hence offers improved operability.

BRIEF DESCRIPTION OF THE DRAWINGS

This and other objects and features of the present invention will become clear from the following description taken in conjunction with the preferred embodiments thereof with reference to the accompanying drawings.

DETAILED DESCRIPTION OF THE PREFERRED EMBODIMENTS

Before the description of each of the preferred embodiments according to the present invention proceeds, it is to be noted that like or corresponding parts are designated by like reference numerals throughout the accompanying drawings.

A detailed description is made below upon dental filling instruments and attachments of the preferred embodiments, with reference to FIG. 3 through FIG. 12B.

Figure 3:
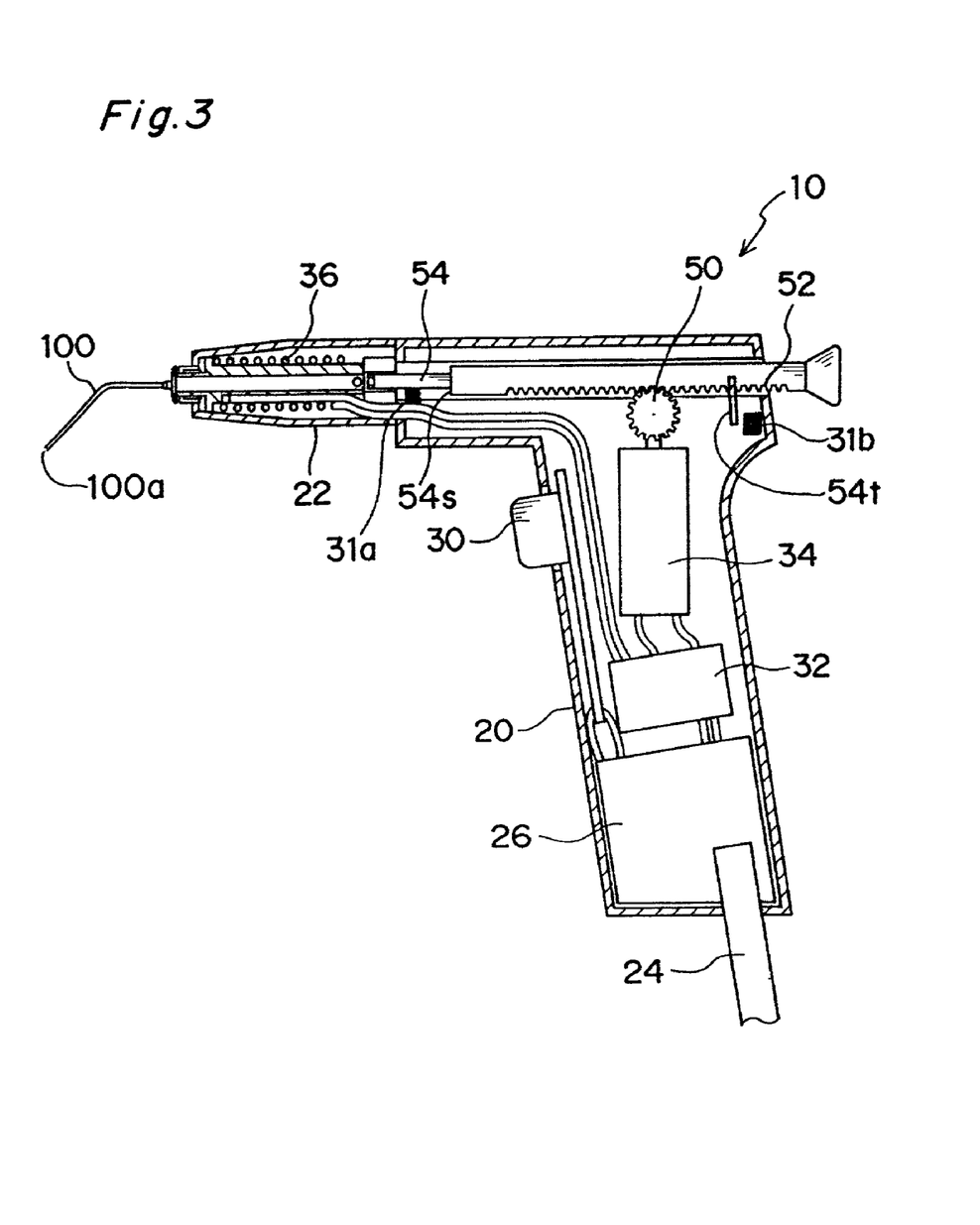
FIG. 3 is a sectional view showing a dental filling instrument as a first embodiment of the present invention.

Referring first to FIG. 3, it is explained about a dental filling instrument 10 of a first embodiment of the present invention.

The dental filling instrument 10 includes a housing 20 substantially gun-shaped so as to allow the user to hold it with one hand, and a needle 100 having a tip 100a from which a dental filler, such as gutta-percha, softened by heating, is extruded when an extruding operation switch 30 is turned ON.

More specifically, the housing 20 has an upper portion accommodating therein a heater 36 for heating a filler and an extruding shaft 54 for extruding the filler. For heat insulation the heater 36 of the housing 20 is surrounded by a thermal protector 22. The extruding shaft 54 is formed with a rack 52 adapted to mesh with a gear 50 (schematically shown). The housing 20 has a lower portion accommodating therein a motor 34 for driving the gear 50, a control board 32 carrying a control circuit for controlling the heater 36 and the motor 34, the extruding operation switch 30 that can be turned ON by depressing an exposed portion protruding out of the housing 20, and a power supply board 26 connected to a power supply cord 24 for supplying electric power to the control board 32.

The dental filling instrument 10 is loaded with a filler, which in turn is softened by heating with the heater 36. When the user holding the lower portion of the housing 20 with on hand depresses the extruding operation switch 30 with a finger, the motor 34 starts rotating the gear 50. The rack 52 meshing with the gear 50 causes the extruding shaft 54 to move the filler in the extruding direction (leftward in FIG. 3). Thus, the filler softened by heating is pushed toward the needle 100 and extruded outside from the tip 100a of the needle 100.

When a returning operation switch not shown is turned ON, the motor 34 revolves in reverse, causing the extruding shaft 54 to travel in the direction opposite from the extruding direction. Thus, the user is no longer required to pull back the extruding shaft 54 once moved in the filler extruding direction with hand and hence becomes capable of performing the filling operation conveniently.

For the sake of safety, the dental filling instrument 10 has a first limit switch 31a and a second limit switch 31b in the housing 20 as shown in FIG. 3, the first switch 31a being adapted to detect a leading terminal of the extruding shaft 54 traveling in the extruding direction, the second limit switch 31b being adapted to detect a rear terminal of the extruding shaft 54 traveling in the returning direction. More specifically, when the motor 34 revolves forward to cause the extruding shaft 54 to travel in the extruding direction (leftward in the drawing) until a shoulder portion 54s of the extruding shaft 54 is brought into contact with the limit switch 31a, the motor 34 stops revolving to stop movement of the extruding shaft 54 at the leading terminal in the extruding direction. On the other hand, when the motor 34 revolves in reverse to cause the extruding shaft 54 to travel in the opposite direction (rightward in the drawing) until a detection plate 54t attached to the extruding shaft 54 is brought into contact with the limit switch 31b, the motor 34 stops movement of revolving to stop movement of the extruding shaft 54 at the rear terminal in the returning direction.

The dental filling instrument 10 operates in any one of the following operating modes when the extruding operation switch 30 is depressed. It is to be noted that the operating mode of the dental filling instrument 10 may be fixed or may be freely selected.

In a first operating mode, when the extruding operation switch 30 is depressed, the motor 34 revolves at a fixed speed so that the extruding shaft 50 travels at a predetermined speed. Accordingly, the filler is extruded at a constant speed from the tip 100a of the needle 100 thereby ensuring a stabilized filling operation.

In a second operating mode, when the extruding operation switch 30 is depressed, the motor 34 revolves until a predetermined number of revolutions is reached so that the extrusion shaft 50 travels a predetermined distance. Accordingly, a predetermined amount of the filler is extruded from the tip 100a of the needle 100. Since the amount of the filler to be extruded does not exceed the predetermined amount, it is possible to minimize the overflow of the filler even if it occurs as shown in FIG. 2.

In a third operating mode, when the extruding operation switch 30 is depressed, the motor 30 revolves for a predetermined time period so that the extruding shaft 50 travels for a predetermined time period. Accordingly, the filler is extruded from the tip 100a of the needle 100 for a limited and predetermined time period. Since the filler is extruded for a limited time period after the extruding operation switch 30 is turned ON, the amount of the filler extruded does not exceed a predetermined amount and, hence, it is possible to minimize the overflow of the filler even if it occurs as shown in FIG. 2.

In a fourth operating mode, the motor 34 revolves during only a time period for which the extruding operation switch 30 is depressed. When the user stops depressing the extruding operation switch 30, the motor 34 stops revolving. Since the filler is extruded in response to an operation depressing the extruding operation switch 30, the user becomes capable of performing the filling operation intuitively.

The fourth operating mode may be combined with any one of the first to third operating modes. In this case, the fourth operating mode should take precedence over any other operating mode. That is, a configuration should be employed such that that the motor 34 stops revolving when the user stops depressing the extruding operation switch 30 even if the condition for terminating the operation in any one of the first to third operating modes is not satisfied.

In any one of the operating modes, the motor 34 revolves forward to extrude the filler. The revolution of the motor 34 is stopped to stop the extrusion of the filler. Since the extruding pressure remains for a while even though the motor 34 stops revolving, the filler continues to be extruded from the tip 100a of the needle 100 for a while after the revolution of the motor 34 has been stopped.

To stop the extrusion of the filler completely, it is preferred that the motor 34 revolving forward be reversed for a predetermined time period and then stopped. Accordingly, the extrusion of the filler from the tip 100a of the needle 100 is stopped immediately after the operation of stopping the filling and, hence, the filling operation, as a whole, is facilitated. Further, it is possible to accurately control the amount of the filler used.

Preferably, the returning operation switch takes precedence over the extruding operation switch 30. That is, when the returning operation switch is turned ON, the extrusion of the filler is stopped even if the extruding operation switch 30 is in an ON state.

Next, description is made on variations (modifications) of the dental filling instrument 10 by focusing the features different from those of the instrument 10.

Figure 4:
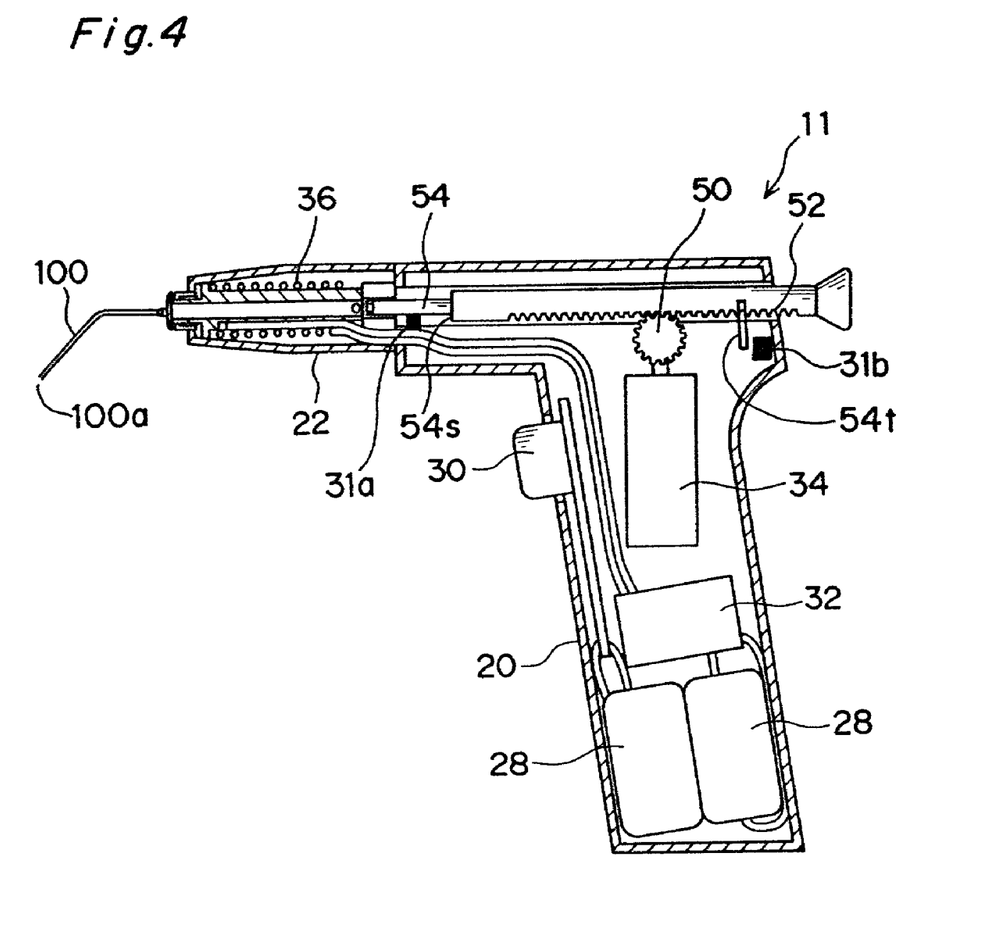
FIG. 4 is a sectional view showing a variation of the dental filling instrument shown in FIG. 3.

As shown in the sectional view of FIG. 4, a dental filling instrument 11 as a first variation of the dental filling instrument 10 is configured to accommodate a power supply battery 28 in the housing 20 instead of supplying power through the power supply cord 24. Elimination of the power supply cord 24 facilitates the handling of the dental filling instrument 11.

Figure 5A:
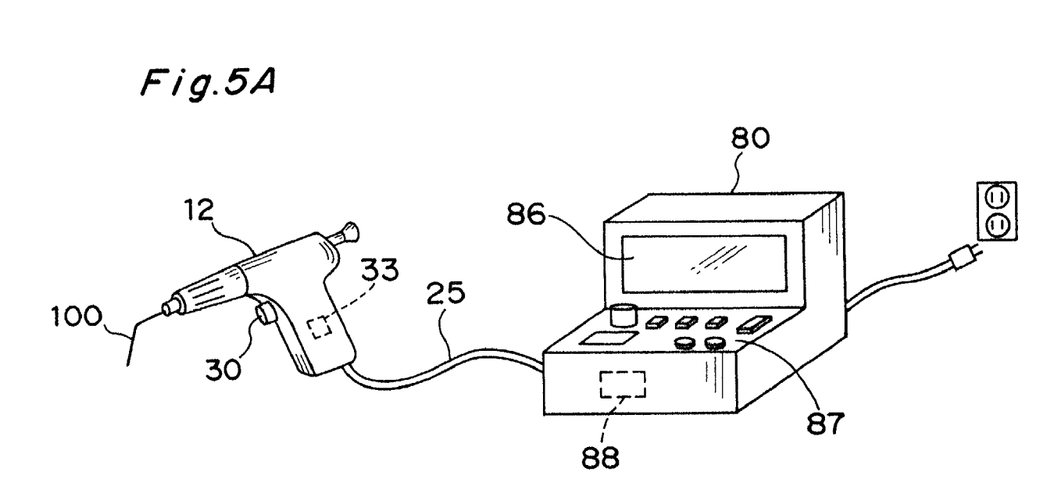
FIGS. 5A and 5B are schematic views showing the configurations of other variations of the dental filling instrument shown in FIG. 3.

A second variation as shown in FIG. 5A comprises a dental filling instrument 12 and a main box 80, which are connected to each other through a connection cable 25.

The dental filling instrument 12 is of substantially the same construction as that of the dental filling instrument 10 shown in FIG. 3, but differs from the instrument 10 in that a control board 33 communicates with a control board 88 located in the main box 80 to be described later through the connection cable 25. The connection cable 25 serves to supply electric power to the dental filling instrument 12 while transmitting signals between the dental filling instrument 12 and the main box 80.

The main box 80 includes a display section 86, a control console 87 and the control board 88.

Various settings in relation to the operation of the dental filling instrument 12 can be made by appropriately operating switches and volume control buttons on the control console 87. The console 87 allows appropriate setting of, for example, the filler injecting conditions including filler extruding amount (the amount of the filler to be injected), time (injection time) and speed (injection speed) and the heating conditions including filler heating temperature (heating temperature) and heating time. Such a configuration is possible that the injection speed, calculation of which is cumbersome, is automatically set once the filler injecting amount and injection time, which are easy to predetermine, are set previously.

The display section 86 appropriately displays numerical values or pictures representing various conditions set at the control console 87 (injecting conditions and heating conditions) or the current state of the dental filling instrument 12 (standby state for filler loading, temperature of the filler heated, filler heating terminated state, amount of the filler filled, filler injection terminated state, or the like). For example, the display section 86 displays a schematic illustration of a root canal and shows a varying region in the illustrated root canal shown with varying amount of the filler injected.

Figure 5B:
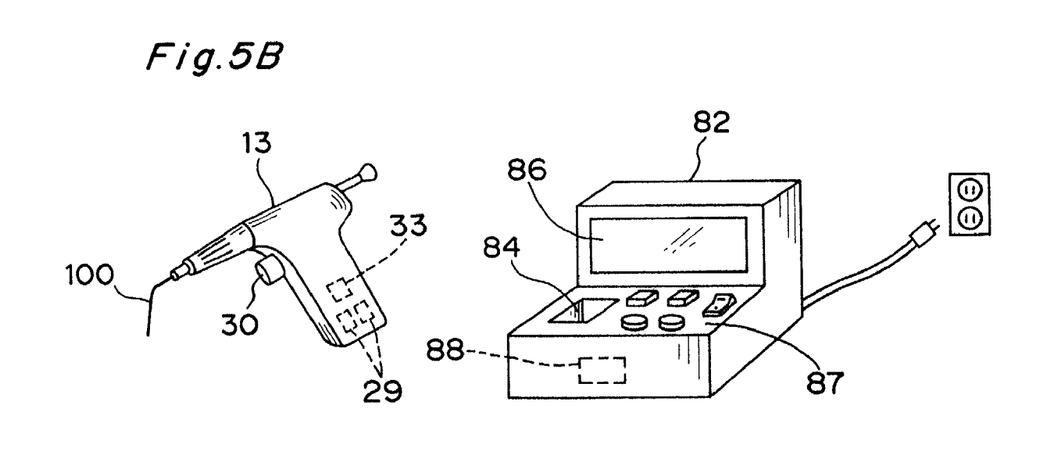

A third variation as shown in FIG. 5B is of substantially the same construction as that of the second variation, but differs from the second variation in that a main box 82 is provided with a dental filling instrument rest 84 for a dental filling instrument 13 to rest thereon and the connection cable 25 is eliminated. More specifically, the rest 84 of the main box 82 is provided with a charger terminal and a signal terminal. On the other hand, the dental filling instrument 13 has a chargeable battery 29 and a terminal not shown. The battery 29 is charged while the dental filling instrument 13 rests on the rest 84 of the main box 82. Communication between a control section 88 of the main box 82 and the control board 33 of the dental filling instrument 13 is possible.

Next, with reference to FIGS. 6 to 9F, a dental filling instrument of a second embodiment of the present invention is described below.

Figure 6:
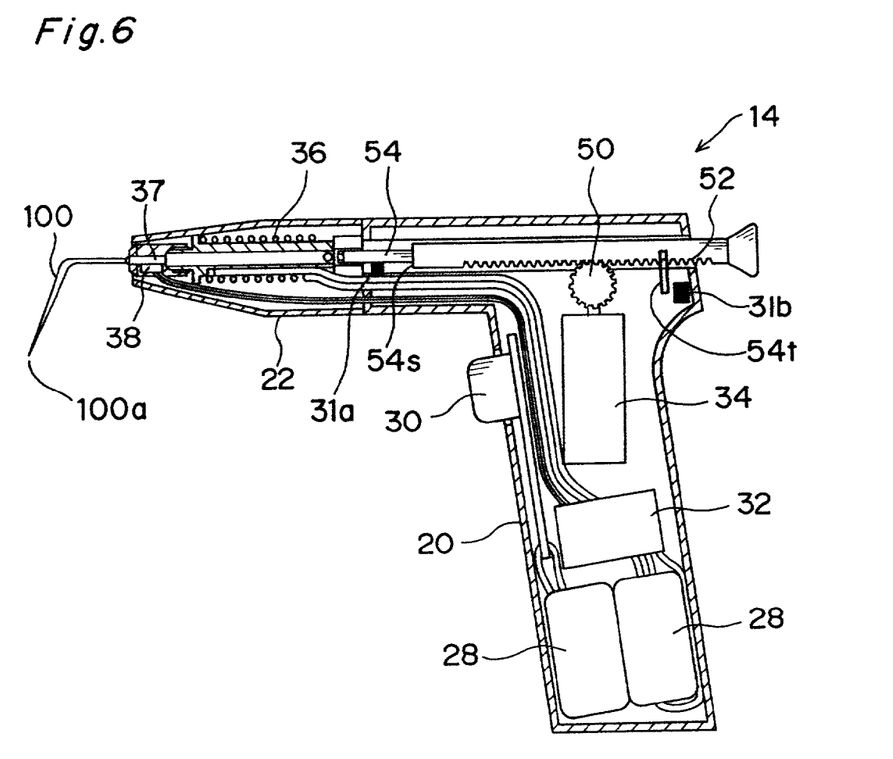
FIG. 6 is a sectional view showing a dental filling instrument as a second embodiment of the present invention.

The dental filling instrument 14 according to the second embodiment is of substantially the same construction as that of the dental filling instrument 10. The features of the instrument 14 different from those of the instrument 10 are focused in the following description.

Figure 7:
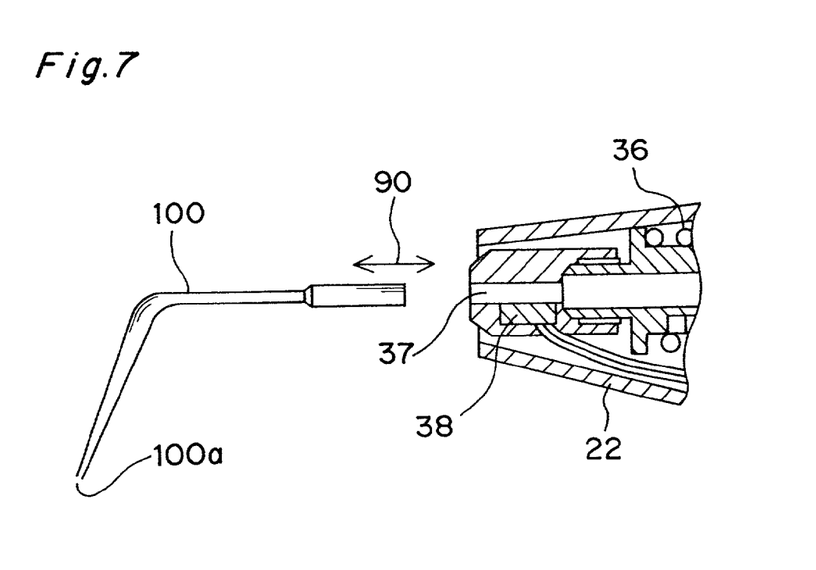
FIG. 7 is an enlarged fragmentary view showing a relevant portion of the dental filling instrument shown in FIG. 6.

As shown in the sectional view of FIG. 6 and in the enlarged fragmentary view of FIG. 7, the dental filling instrument 14 includes a heater 38 adjacent a needle fitting portion 37. The heater 38, which is separate from and independent of the heater 36 adapted to heat the filler, is adapted to heat the base end of the needle 100. The needle fitting portion 37 allows a spreader- or plugger-type attachment (to be described later) to be fitted thereto instead of the needle 100. It is desirable that the instrument be modified in its outward shape from the substantially T-shaped gun type into a substantially I-shaped hand piece type for improved operability.

It is desirable that the heating temperature of the heater 38 be controlled independently of the heater 36 adapted to heat the filler. This is because the needle or attachment fitted to the needling fitting portion 37 can be easily heated to a desired temperature. In this case the heating temperature of the heater 38 may be set independently of the heater 36 by a temperature setting section not shown. Desirably, the heating temperature of the heater 38 thus set is displayed in a temperature display section not shown.

Figure 8A:
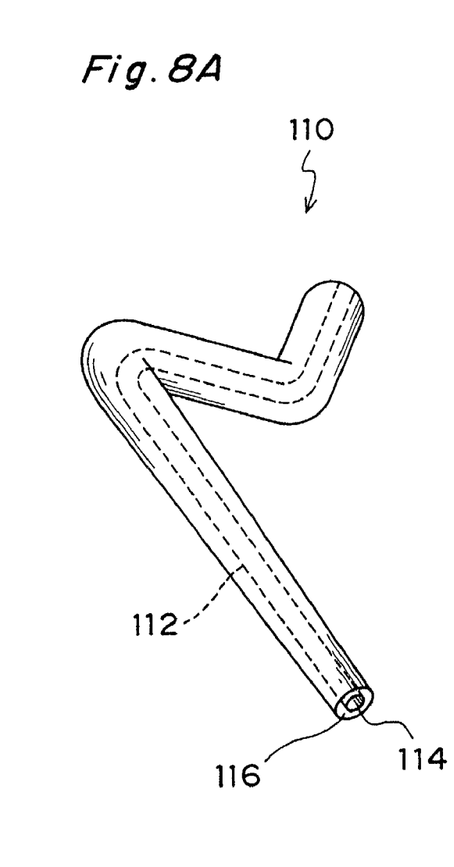
FIGS. 8A, 8B and 8C are perspective views showing plugger-type attachments.
Figure 8B:
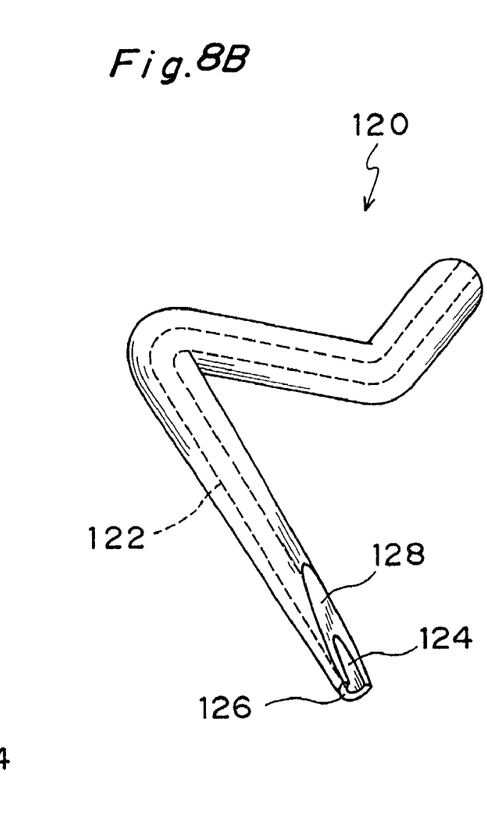
Figure 8C:
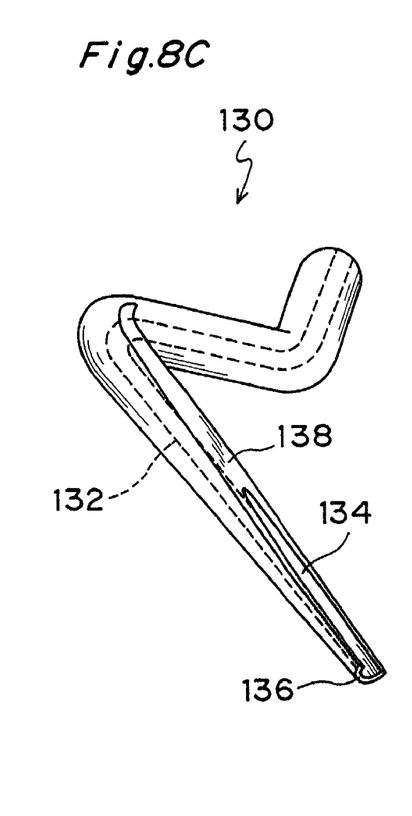

FIGS. 8A to 8C illustrate examples of plugger-type attachments. These attachments 110, 120 and 130 define bores 112, 122 and 132, respectively, and each can be used as a needle through which a filler is extruded, as well as a plugger.

The attachment 110 shown in FIG. 8A has a flat tip 116 defining a circular opening 114. The attachment 120 shown in FIG. 8B has a tip 126 cut to form an inclined surface 128 defining a larger opening 124. The attachment 130 shown in FIG. 8C has a tip 136 cut to form a larger inclined surface 138 defining a much larger opening 134.

When any appropriate one of these attachments 110, 120 and 130 is selected and attached to the filling instrument 14, it is possible to cut a previously inserted root canal plug by burning with the attached attachment heated with the heater 38 and then to fill the root canal with a dental filler. Since the filling operation can be performed without exchanging the attachment or needle attached to the filling instrument 14, it is possible to perform required operations continuously and efficiently.

FIGS. 9A to 9F illustrate examples of spreader-type attachments. These attachments 210, 220 and 230 define bores 212, 222 and 232, respectively, and each can be used as a needle through which a filler is extruded, as well as a spreader.

Figure 9A:
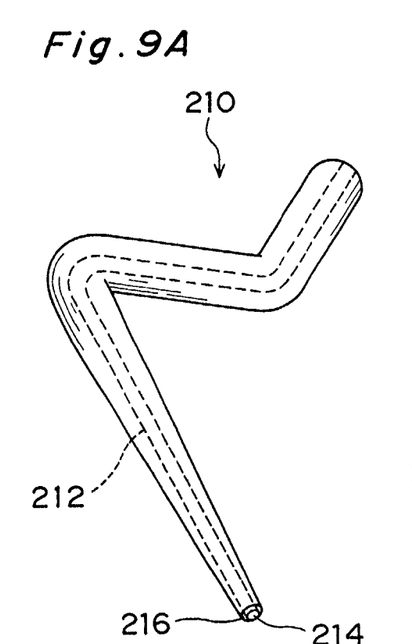
FIGS. 9A to 9F are perspective views showing spreader-type attachments.
Figure 9B:
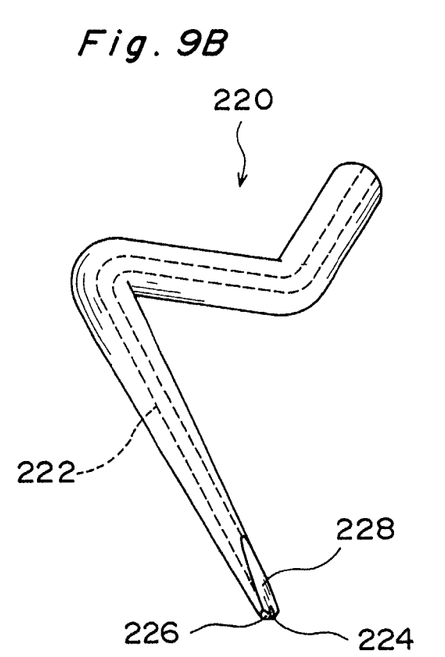
Figure 9C:
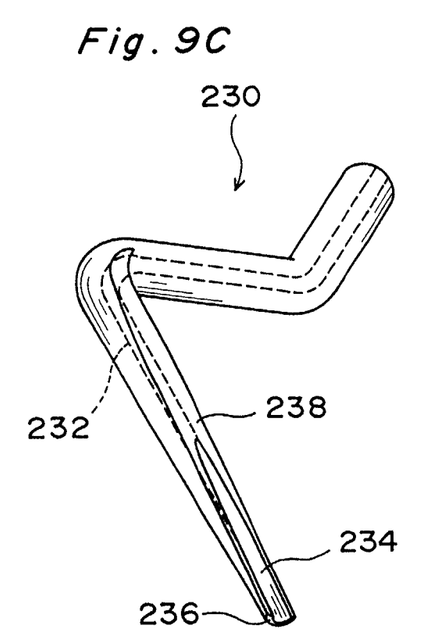
Figure 9D:
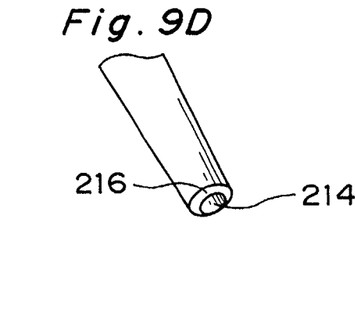
Figure 9E:
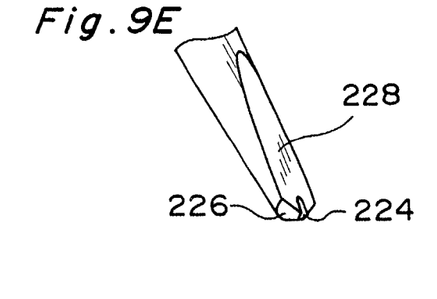
Figure 9F:
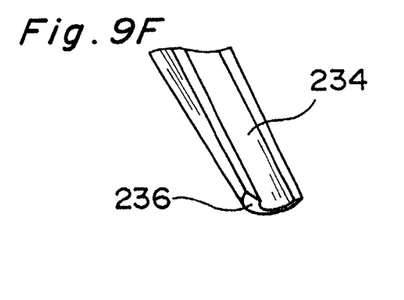

The attachment 210 shown in FIG. 9A has a tip 216 formed into a curved surface defining a circular opening 214 as better shown in the enlarged fragmentary view of FIG. 9D. The attachment 220 shown in FIG. 9B has a tip 226 cut to form an inclined surface 228 defining a larger opening 224 as better shown in the enlarged fragmentary view at FIG. 9E. The attachment 230 shown in FIG. 9C has a tip 236 cut to form a larger inclined surface 238 defining a much larger opening 234 as better shown in the enlarged fragmentary view at FIG. 9F.

When any appropriate one of these attachments 210, 220 and 230 is selected and attached to the filling instrument 14, it is possible to cut a previously inserted root canal plug by burning with the attached attachment heated with the heater 38 and then fill the root canal with a dental filler. Since the operations of treating the plug and injecting the filler can be performed without exchanging the attachment or needle attached to the filling instrument 14, it is possible to perform required operations continuously and efficiently.

Next, with reference to FIGS. 10 to 12, a dental filling instrument of a third embodiment of the present invention is described below.

The dental filling instrument according to the third embodiment is of substantially the same construction as that of the first embodiment, but has a different filler magazine.

Figure 10:
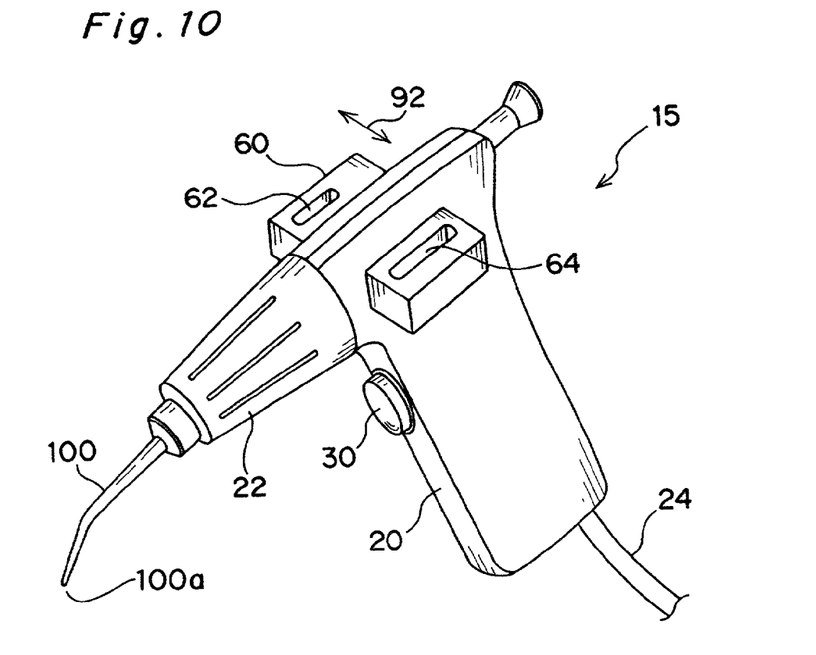
FIG. 10 is a perspective view showing a dental filling instrument as a third embodiment of the present invention.

Specifically, dental filling instrument 15 shown in FIG. 10 includes a filler magazine 60 slidably supported by an upper portion of the housing 20. The filler magazine 60 has a filler storage sections 62 and 64 in portions outwardly protruding on opposite sides of the housing. When the magazine 60 slides to the right or left in the direction indicated by an arrow 92, the filler in the filler storage section 62 or 64 is introduced into the housing 20 and hence becomes ready to be used in the filling operation.

For example, it is possible that a filler for filling apical part is stored in the filler storage section 62 on one side while a common filler for filling whole root canal is stored in the filler storage section 64 on the other side. In this case, it is desirable that the filler storage section 62 be sized to store an amount (0.01 ml for example) of the filler estimated from the volume of an apical part, while the filler storage section 64 be sized to store an amount (0.09 ml for example) of the filler estimated from the volume of a whole root canal. It is also desirable that the filler for filling apical part be of a low-temperature-melting type which melts at 60° C. (degrees Celsius) for example, while the common filler be of a high-temperature-melting type which melts at 160° C. for example.

Once predetermined fillers are stored in respective filler storage sections 62 and 64, the filler magazine 60 is slid toward the proximal side of the viewer of FIG. 10 to place one filler storage section 62 into the housing 20. The filler in the filler storage section 62 thus placed in the housing 20 is heated to a temperature previously set (60° C. for example) with the heater. At this time the needle 100 may also be heated with the heater.

Subsequently, the extruding operation switch 30 is turned ON to extrude the filler from the tip 100*a* of the needle 100 for an apical part to be filled with the filler.

In turn, the filler magazine 60 is slid toward the opposite side (toward the distal side of the viewer of FIG. 10) to place the other filler storage section 64 into the housing 20. The filler in the filler storage section 64 thus placed in the housing 20 is automatically heated to a temperature previously set (160° C. for example). At this time the needle 100 may also be heated with the heater. Subsequently, the extruding operation switch 30 is turned ON to extrude the filler from the tip 100*a* of the needle 100 for a whole root canal to be filled with the filler.

It is desirable that at least one of the extruding and heating conditions including filler heating temperature, heating time and extruding amount be previously set for each of the filler storage sections 62 and 64. In this case a configuration may be employed such as to allow the heating and extruding conditions to be appropriately set from a control console of a main box (not shown) connected to the dental filling instrument 15.

In the case where the heating temperature or the heating time for one filler is different from that for another filler, a configuration may be employed such as to notify the user of the termination of filler heating (i.e., the state ready to perform the filling operation) by means of sound or display upon completion of filler heating.

Figure 11:
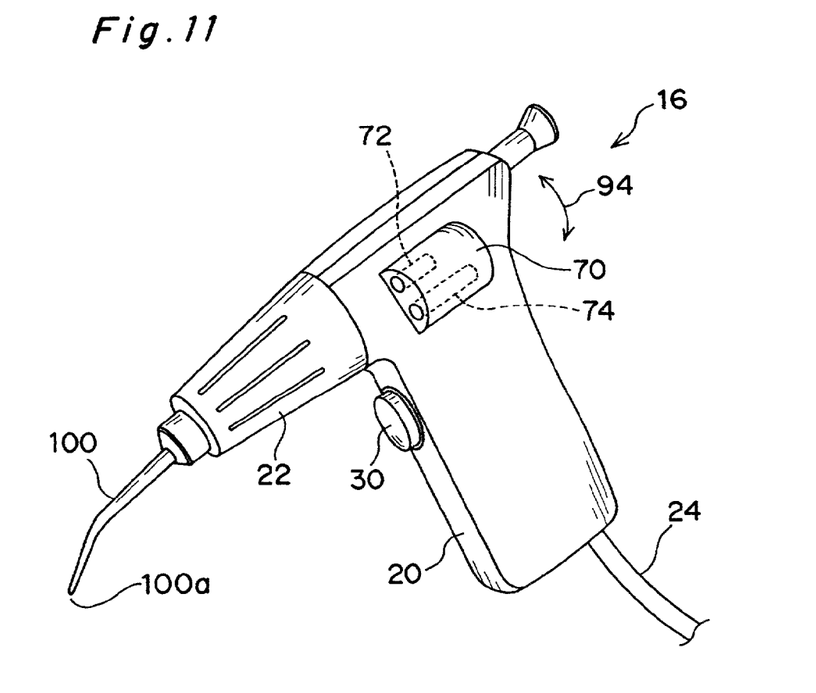
FIG. 11 is a perspective view showing a variation of the dental filling instrument shown in FIG. 10.

FIG. 11 illustrates a dental filling instrument 16 as a variation (or modification) of the dental filling instrument 15. The dental filling instrument 16 includes a filler magazine 70 rotatably supported by an upper portion of the housing 20 and having filler storage sections 72 and 74 for storing fillers in a portion protruding on one side of the housing 20. The filler to be introduced into the housing 20 can be selected by rotating the magazine 70 in the direction indicated by an arrow 94.

Figure 12A:
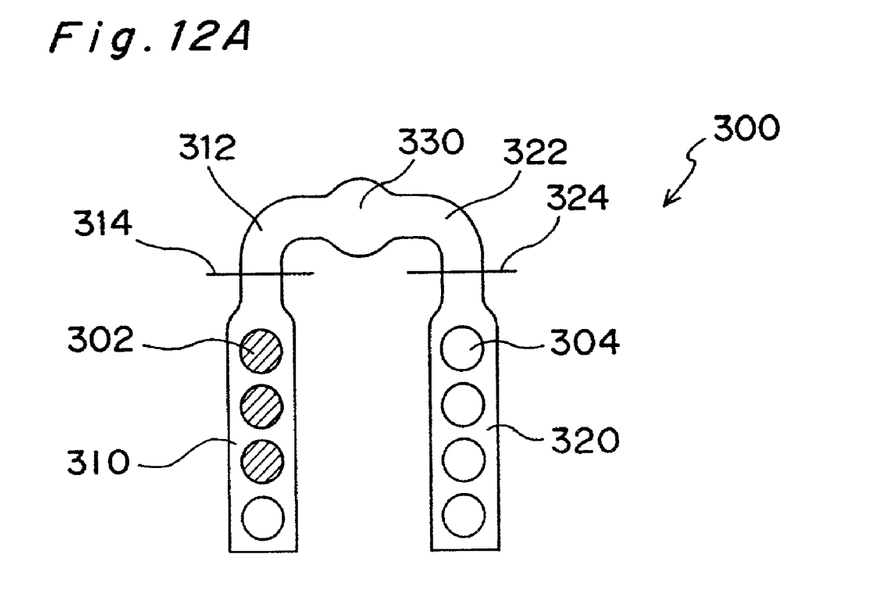
FIGS. 12A and 12B are schematic views showing a feature of another variation of the dental filling instrument shown in FIG. 10.
Figure 12B:
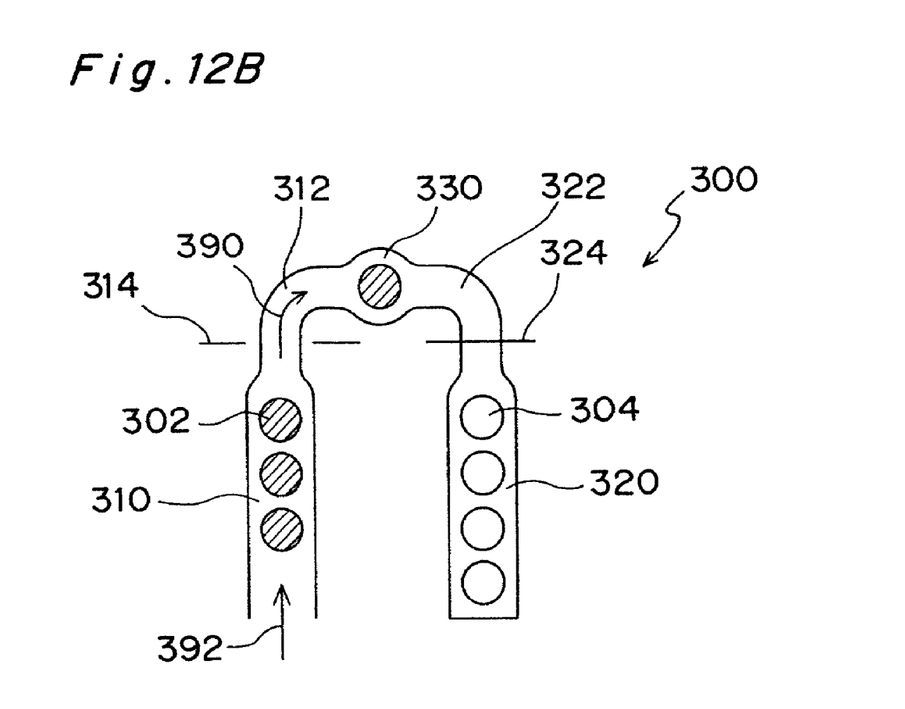

FIG. 12 schematically illustrates a feature of another variation of the dental filling instrument 15. As shown in FIG. 12A, a filler magazine 300 has two filler storage sections 310 and 320 for storing plural fillers 302 and 304, a loading section 330, communicating sections 312 and 322 providing communication between the loading portion 330 and the filler storage sections 310 and 320, and shutters 314 and 324 disposed in the communicating sections 312 and 322, respectively. When one shutter 314 is opened as shown in FIG. 12B, the filler 302 in the filler storage section 310 is urged in the direction indicated by an arrow 392 by means of an urging mechanism not shown and transferred to the loading portion 330 along an arrow 390.

Use of any one of the foregoing dental filling instruments makes it possible to fill a tooth cavity with a filler more easily.

Although the present invention has been fully described in connection with the preferred embodiments thereof with reference to the accompanying drawings, it is to be noted that various changes and modifications are also apparent to those skilled in the art.

For example, though in the above description, an explanation about a sealer for improving the adhesion between a root canal and a filler is skipped, the present invention does not inhibit the use of such a sealer but permits appropriate use of such a sealer. It is needless to say that use of a root canal length measuring instrument in cooperation is more desirable.

Dental fillers in the present invention may be used without being heated with the heater of the dental filling instrument. For example, a resin which does not require heating for softening it may be used as a filler, or the dental filling instrument may be loaded with a filler previously softened by heating with a separate heater.

It is possible to employ a configuration to allow the whole heater section to be replaced by another in order to vary the heating temperature. Further, the filler magazine or holder for storing fillers therein may be configured to be replaceable with another one.

What is claimed is:

1. A dental filling instrument comprising:
   a housing, said housing including:
      a push rod for extruding a dental filler;
      an electric drive motor for a push rod driving device for performing a dental filler extruding operation that causes the push rod to travel in a dental filler extruding direction coupled to and utilizing power of an electric power source;
      a control circuit means for controlling the dental filler extruding operation of the electric drive motor, said control circuit means being provided in said housing;
      an injection condition setting device for setting at least one of an amount of the dental filler to be injected, filler injection time and injection speed of the dental filler;
      an injection condition display device for displaying at least one of an amount of the dental filler to be injected, filler injection time and injection speed of the dental filler;
      a needle from which said dental filler is extruded fitted to a needle fitting portion of said housing;
      a heating device for heating the needle up to a temperature at which the dental filler is softened, the heating device being disposed at one of the needle fitting portion and a location adjacent to the needle fitting portion;
      a heating temperature setting device for setting the temperature up to which the needle is heated by the heating device; and
      a heating control device for controlling a heating operation of the heating device based on the temperature set by the heating temperature setting device; and
   wherein:
      the control circuit means includes:
         a traveling speed control section for controlling traveling speed of the push rod;
         a traveling distance control section for controlling distance which the push rod travels; and a traveling time control section for controlling traveling time of the push rod; and the control device controls the dental filler extruding operation of the push rod driving device based on the injection condition set by the injection condition setting device.

2. The dental filling instrument as claimed in claim 1, in which the control device includes an extruding operation switch and a control section responsive to the extruding operation switch, wherein when the extruding operation switch is in an ON state, the control section responsive to the extruding operation switch permits the push rod driving device to perform the dental filler extruding operation, and wherein when the extruding operation switch is in an OFF state, the control section forcibly inhibits the push rod driving device from operating.

3. The dental filling instrument as claimed in claim 1, in which the push rod driving device is capable of performing a push rod returning operation that causes the push rod to travel in a direction opposite to the dental filler extruding direction by utilizing the power of the power source, wherein the control device includes a returning operation switch and a control section responsive to the returning operation switch, and wherein when the returning operation switch is in an ON state, the control section responsive to the returning operation switch forcibly inhibits the push rod driving device from performing the dental filler extruding operation while permitting the push rod driving device to perform the push rod returning operation.

4. The dental filling instrument as claimed in claim 3, in which the control device includes an extrusion stop control section for causing the push rod driving device to perform the returning operation for a predetermined time period immediately after the dental filler extruding operation of the push rod driving device has been stopped.

5. The dental filling instrument as claimed in claim 1, wherein the push rod driving device is capable of performing a push rod returning operation that causes the push rod to travel in a direction opposite to the dental filler extruding direction by utilizing the power of the power source, and wherein the control device includes:

a terminating point detection device for detecting the push rod reaching a first predetermined position in the dental filler extruding direction;

a starting point detection device for detecting the push rod reaching a second predetermined position in a direction the opposite to the dental fillet extruding direction; and a push rod traveling range control section for forcibly inhibiting the push rod driving device from performing the dental filler extruding operation when the terminating point detection device detects the push rod reaching the first predetermined position, and for forcibly inhibiting the push rod driving device from performing the push rod returning operation when the starting point detection device detects the push rod reaching the second predetermined position.

6. The dental filling instrument as claimed in claim 1, which includes a housing shaped to allow a user to hold it with one hand, and wherein all other components are provided in one of a location which corresponds to an inside of the housing, and a location which corresponds to an outer surface of the housing.

7. The dental filling instrument as claimed in claim 1, which includes a heating temperature display device for displaying the temperature of said needle set by the heating temperature setting device.

8. The dental filling instrument according to claim 1, further comprising:

a main body of said housing; and wherein said needle fitting portion is provided in the main body, for attaching a needle, so as to extrude a dental filler from a tip of the needle, wherein the needle fitting portion is capable of being fitted with an attachment of one of the spreader type and the plugger type.

9. The dental filling instrument as claimed in claim 8, in which a heater is included in one of the needle fitting portion and a portion adjacent to the needle fitting portion.

10. The dental filling instrument as claimed in claim 8, in which the needle fitting portion is fitted with the attachment having a first end attached to the needle fining portion and a second end and defining a through-hole extending therethrough from the first end to the second end.

11. The dental filling instrument as claimed in claim 8, in which the needle fitting portion is capable of being fitted with the attachment formed from a superelastic alloy.

12. The dental filling instrument as claimed in claim 8, wherein said housing is shaped to allow a user to hold it with one band, and all other components are provided in one of a location which corresponds to an inside of the housing, and a location which corresponds to an outer surface of the housing.

13. The dental filling instrument according to claim 1, further comprising:

a body of said housing; and an attaching portion, provided in the body, for attaching to a needle fitting portion of said dental filling instrument for extruding a dental filler from a tip of a needle attached to the needle fitting portion thereof.

14. The dental filling instrument as claimed in claim 13, wherein said attaching portion includes a first end attached to the needle fitting portion and a second end, and a through-hole extending therethrough from the first end to the second end.

15. The dental filling instrument as claimed in claim 13, wherein the needle of said attaching portion is made of a superelastic alloy.

16. The dental filling instrument as claimed in claim 1, wherein said housing includes an electric power source and said electric power source is a rechargeable battery means provided in said housing.

17. The dental filling instrument as claimed by claim 1 which further includes a filler magazine slidably supported by an upper portion of the housing and a plurality of filler storage sections provided in the filler magazine in portions of the filler magazines outwardly protruding on opposite sides of the housing.

18. The dental filling instrument according to claim 1 further comprising a filler magazine comprising a cylinder rotatably supported by an upper portion of the housing and a plurality of filler storage sections provided in said cylinder for storing fillers in portions of said cylinder on one side of the housing.

* * * * *